United States Patent [19]
Johnson et al.

[11] Patent Number: 5,531,959
[45] Date of Patent: Jul. 2, 1996

[54] AUTOMATED LIQUID HANDLING AND COMPUTER CONTROLLED SYSTEM AND METHOD FOR SOLID PHASE CHROMATOGRAPHIC EXTRACTIONS

[75] Inventors: James E. Johnson; Christopher B. Shumate; Andy W. Siu; Ronald Gundlach, all of Reno, Nev.

[73] Assignee: Hamilton Company, Reno, Nev.

[21] Appl. No.: 381,559

[22] Filed: Jan. 31, 1994

[51] Int. Cl.⁶ ................................................ G01N 30/02
[52] U.S. Cl. .................. 422/70; 73/61.56; 96/19; 96/22; 96/23; 96/102; 210/198.2; 210/656; 210/739; 210/741; 422/62; 422/81; 422/89; 422/101; 436/161
[58] Field of Search .................... 422/81, 70, 89, 422/62, 68.1, 101; 73/61.56; 210/656, 198.2, 739, 741; 436/177, 178, 161; 96/19, 22, 23, 102

[56] References Cited

U.S. PATENT DOCUMENTS

| | | | |
|---|---|---|---|
| 3,632,119 | 1/1972 | Carpenter | 277/26 |
| 3,912,456 | 10/1975 | Young | 23/253 |
| 4,677,987 | 7/1987 | Choksi | 128/719 |
| 4,678,752 | 7/1987 | Thorne et al. | 435/291 |
| 4,679,446 | 7/1987 | Sheehan et al. | 73/864.13 |
| 4,730,631 | 3/1988 | Schwartz | 134/155 |
| 4,832,882 | 5/1989 | Moylan | 210/741 |
| 4,840,730 | 6/1989 | Saxena | 218/198.2 |
| 4,976,750 | 12/1990 | Munari | 55/21 |
| 4,980,297 | 12/1990 | Haynes et al. | 436/178 |
| 4,994,096 | 2/1991 | Klein et al. | 55/21 |
| 5,078,970 | 1/1992 | Teodorescu et al. | 422/100 |
| 5,079,170 | 1/1992 | Rosman et al. | 436/178 |
| 5,169,120 | 12/1992 | Guthrie, Jr. et al. | 251/122 |
| 5,322,626 | 6/1994 | Frank et al. | 210/634 |
| 5,324,480 | 6/1994 | Shumate et al. | 422/63 |

OTHER PUBLICATIONS

Kloehn Company, Kloehn Micro Syringes Catalog, 1987, entire catalog.
Scientific Glass Engineering, Scientific Glass Engineering product catalog, 1984, pp. 42, 43, 48, 49, 64, 65 and 73.

*Primary Examiner*—Jill Warden
*Assistant Examiner*—Jan M. Ludlow
*Attorney, Agent, or Firm*—Bernhard Kreten

[57] ABSTRACT

A method and apparatus for solid phase extraction chromatography is disclosed in which the flow rate of a fluid, such as the motive pressurized gas is monitored, adjusted and compared with a standardized pressure curve which is correlative of a sample being processed. By monitoring and adjusting changes in flow rate, which can correspond to process initialization, beginning, ending and key fractionating points, and correlating to a standard, the cycle time for assaying the sample in question can be maximized and multiple samples can pass through analysis automatically and quickly.

14 Claims, 5 Drawing Sheets

AUTOMATED LIQUID HANDLING AND COMPUTER CONTROLLED SYSTEM AND METHOD FOR SOLID PHASE CHROMATOGRAPHIC EXTRACTIONS

FIELD OF THE INVENTION

The invention relates generally to a liquid handling system used in chemical analysis, and in particular, to a flow control system for automatically monitoring and optimizing fluid flow in the multiple steps involved in chromatographic assaying.

BACKGROUND OF THE INVENTION

The following invention reflects ongoing advancement and evolution concerning applicant's earlier U.S. Pat. No. 5,324,480, issued Jun. 28, 1994.

Sample preparations in industrial research and clinical laboratories require many precise pipetting steps, such as: transfer of samples, dilutions, additions of reagents, transfer of reaction mixtures, etc. Automated systems have been developed and are commercially available in the form of programmable pipetting workstations. These automated systems reduce the manual labor involved in the liquid handling and processing of samples.

However, these systems are not completely automatic, because, among other things, they still require manual manipulation of gas regulators in order to provide a specific pressure at appropriate times in the protocol for processing samples.

For example, solid phase extraction often requires multiple steps such as column conditioning, sample loading, washing and elution. Depending on the application, the solvents and samples involved may have different viscosities, different particulate composition and, depending on the protocol step, may require different pressures. The ability to precisely provide and control the various ranges of pressure required during the protocol steps is critical in obtaining good recovery and throughput in the process of solid phase extraction. For example, the loading and elution of samples is typically carried out at low pressure while various other steps are carried out at higher rates of pressure. Existing systems are unable to completely automate and control the various ranges of pressure required in the multiple steps of performing solid phase extraction.

Typically, the user is required to manually operate an air regulator. The regulators have poor accuracy in the middle of the zero to thirty pounds per square inch range and worse accuracy in the critical low pressure range (0 to 2 pounds per square inch). Typically, the user has a manifold of manual air regulators and starts out with the lowest and slowest air pressure as the global pressure setting for requirements of the specific protocol being carried out. The user then turns the regulators by hand to obtain the appropriate pressure required at the appropriate times in the protocol. The result of this is that the current system is, at best, semi-automated and fails to consistently provide good recoveries and throughput.

Therefore, there is a need for an apparatus and method which would be capable of providing continuously adjustable pressure regulators for providing high flows in the case of washing and drying steps and very low flows for sample addition and elution.

The following prior art reflects the state of the art of which applicant is aware and is included herewith to discharge applicant's acknowledged duty to disclose relevant prior art.

It is stipulated, however, that none of these references teach singly nor render obvious when considered in any conceivable combination the nexus of the instant invention as disclosed in greater detail hereinafter and as particularly claimed.

| U.S. Pat. No. | ISSUE DATE | [0007]INVENTOR |
|---|---|---|
| 3,632,119 | January 4, 1972 | Robert E. Carpenter |
| 3,912,456 | October 14, 1975 | Robert R. Young |
| 4,677,987 | July 7, 1987 | Pradip V. Choksi |
| 4,678,752 | July 7, 1987 | Thorne, et al. |
| 4,679,446 | July 14, 1987 | Sheehan, et al. |
| 4,730,631 | March 15, 1988 | Henry L. Schwartz |
| 4,980,297 | December 25, 1990 | Haynes, et al. |
| 5,078,970 | January 7, 1992 | Teodorescu, et al. |
| 5,079,170 | January 7, 1992 | Rosman, et al. |
| 5,169,120 | December 8, 1992 | Guthrie, et al. |
| 5,322,626 | June 21, 1994 | Frank, et al. |
| 5,324,480 | June 28, 1994 | Shumate, et al. |

OTHER PRIOR ART (Including Author, Title, Date, Pertinent Pages, Etc.)

Kloehn Company, Kloehn Micro Syringes Catalog, 1987, entire catalog.

Scientific Glass Engineering, Scientific Glass Engineering product catalog, 1984, pages 42, 43, 48, 49, 64, 65 and 73.

The patents to Guthrie, et al. (U.S. Pat. No. 5,169,120) and Frank, et al. (U.S. Pat. No. 5,322,626) teach the use of a supercritical fluid extraction with flow parameters well above the ranges of the instant invention.

Shumate, et al, U.S. Pat. No. 5,324,480 and assigned to applicant teaches the use of an automated extraction device, which, while extremely advantageous to use, does not monitor the flow rate of the pressurized gas which pushes the sample. Instead, a timer sequences events.

The other prior art listed above, but not specifically discussed, further catalog the prior art of which the applicant is aware. These references diverge even more starkly from the references specifically distinguished above.

SUMMARY OF THE INVENTION

The present invention solves the problem of requiring an operator to manually adjust one or more gas regulators throughout a specific protocol. In addition, the present invention eliminates the manual regulators which have poor accuracy and subsequently poor recovery of the constituent in question. This is achieved via an apparatus and method which provides an automatic flow control system which monitors and optimizes gas flow.

High performance solid phase extraction will be the preferred embodiment used in describing the apparatus. In high performance solid phase extraction, a column or tube is packed with a substantially uniform and finely divided stationary phase or barrier, through which a liquid mobile phase, which includes the components to be separated, is pumped under pressure. The flow control system automatically monitors and optimizes the gas flow used to provide the motive force to the liquid phase such that it passes through the solid phase extraction column. Pressure can be momentarily increased to initiate flow of the fluid. In addition, the flow control system can automatically check for clogs and obstructions and determine high flow resistance in the columns and samples. This flow interrogation allows independent processing times for each sample, thereby decreasing the total run time resulting from an arbitrarily and needlessly long pressure pulse being applied via manual gas regulators as was the case heretofore.

The detection of high flow resistance in the columns or samples is extremely significant because columns or samples with a high flow resistance to the mobile fluid will often cause the samples to be improperly processed and subsequently invalidate an entire run. In addition, column drying and hence low recoveries are eliminated by the present invention and precision within runs is greatly increased as a result of the present invention.

While many automated systems promote labor savings, they usually achieve this claim by limiting sample through put, frequently lower than manual operations. The present invention, when provided with a typical automated system, will not only maximize labor, but it will also maximize the throughput and process consistency, while minimizing user intervention.

The flow control system receives its commands from a processor, such as a personal computer, and sends back a response signal correlative to the pressure used to pump the liquid mobile phase past the stationary phase. In addition, the flow control system also provides a differential rate correlative to the change of flow of the liquid through the column. The flow control system is comprised of a digital to analog converter which is connected to an electronic gas regulator. The electronic gas regulator receives gas in from a gas source and exhausts gas out to a mass flow meter. The mass flow meter in turn sends an analog signal to an analog to digital converter which converts the analog signal to a digital signal and transmits the digital signal back to the processor means such as a personal computer. In addition, the flow meter outputs the regulated gas pressure required for the multiple steps in solid phase extraction carried out by the liquid handling system.

The electronic gas regulator of the flow control system operates with a pressure set point which is controlled by the processor means, through a specifically designed software package. A typical range of an electronic gas regulator is between zero and thirty pounds per square inch with an accuracy of 0.1% of the full scale range. Preferably, an eight bit digital signal initiated from the software package provides the user with 255 equal pressure increments throughout the range of the regulator. The electronic gas regulator is electronically controlled through a digital to analog converter. This control is preferably affected through a TTL input-output card cooperating with the processor means and the actual software package protocol.

The electronic gas regulator adjusts throughput as a function of load change, i.e., if the pressure decreases downstream, the regulator increases gas flow to keep the set pressure point; if the pressure increases downstream the regulator decreases flow to keep the set pressure point. Because of this flow change, an effective feedback loop can be achieved through an analog output on a flow meter. This ability to maintain good accuracy at low pressure has led to an increase performance of the programmable pipetting workstation in actual site testing. A second feature of fluid control system is in the monitoring of the flow of gas through the regulator by use of a mass flow meter. A typical range of the mass flow meter is between zero and fifty milliliters per minute. Differential changes in flow can also be observed via an analog output from the mass flow meter. These differential changes are the response signals.

This ability to monitor the state of a column or cartridge is essential to increase through put, safety and ease of operation of a solid phase extraction automated system. The flow control system allows effective monitoring of the liquid through the column whether the cartridge or column is plugged and whether there is a leak in the system. Since liquid flow through solid phase extraction cartridges varies greatly by sample composition and from cartridge to cartridge, the end user will not be constrained, as currently is the practice, by the worst case sample and column. Thus, while one sample might take 120 seconds to process, another may only take 90 seconds.

In addition, the flow control system makes it possible to sense the pressure drop that occurs when the column empties of solvent, thereby allowing an increase in throughput. Moreover, a reduction of the drying of the column prevents loss of recovery of the sample to be assayed. The way a typical systems work now is that all elution times are adjusted to the slowest running column. By sensing when a column is done, many needlessly long waits can be avoided.

OBJECTS OF THE INVENTION

A primary object of the present invention is to provide a new, novel and useful fluid flow control system for a chromatographic system.

A further object of the present invention is to provide a fluid flow control system as characterized above which automatically monitors and optimizes fluid flow during chromatographic processing.

Another further object of the present invention is to provide the fluid flow control system as characterized above which has the capability of automatically checking for clogged solid phase extraction columns.

Another further object of the present invention is to provide the fluid flow control system as characterized above which improves assay reliability.

Another further object of the present invention is to provide a fluid flow control system as characterized above which provides a positive pressure insuring method accuracy, reproducibility and analytical integrity.

Another further object of the present invention is to provide a fluid flow control system as characterized above which may be continuously adjustable thereby allowing high flows in the case of washing and drying steps and very low flows for equilibria dependent sample addition and elution.

Another further object of the present invention is to provide a fluid flow control system as characterized above which can detect high flow resistance in samples and columns and adjust the flow rate accordingly.

Another further object of the present invention is to provide a fluid flow control system which can provide a momentary increase in pressure to initiate the flow through the column.

Another further object of the present invention provides flow interrogation which allows independent processing times and cessation of pressure prior to a dry column scenario for each sample thereby decreasing total run time resulting from an arbitrarily set pressure pulse.

Another further object of the present invention is to provide the status of the column anytime during a run.

Viewed from a first vantage point, it is an object of the present invention to provide a device for sensing the throughput of a sample beyond a barrier in which the sample is initially impeded by the barrier with respect to a detector the device comprising, in combination: a sample holder; the sample and barrier stratified in the sample holder; pressure means addressing the sample; and means to sense motion of constituents of the sample with respect to the barrier.

Viewed from a second vantage point, it is an object of the present invention to provide a method for testing constituents in a sample, the steps including: placing the sample in a holder, applying pressure to the sample, forcing the sample through a medium, gauging a change in the pressure correlative with the throughpassage of the sample, reducing the pressure, and moving to a subsequent sample.

Viewed from a third vantage point, it is an object of the present invention to provide a control system for analyzing fluid flow rate characteristics and supply flow rate data to a flow rate differential analyzer in a chromatograph, comprising: a fluid flow monitor measuring fluid flow through a chromatograph and communicating with the flow rate differential analyzer, a means for varying fluid flow, a means for analyzing changes in the fluid flow rate, the means for varying fluid flow to change flow rate such that when the analyzer means determines all components of a sample have exited the flow rate differential analyzer, a new regimen of analysis steps may be initiated.

Viewed from a fourth vantage point, it is an object of the present invention to provide a method for solid phase extraction of a substance, the steps including: selecting a performance curve correlative of the substance being tested; applying a force to the substance being tested to force the substance into a testing area; comparing the performance curve with a correlative parameter associated with forcing the substance through a resistance medium and into the testing area; and analyzing the substance as it incrementally passes through the testing area.

These and other objects will be made manifest when considering the following detailed specification when taken in conjunction with the appended drawing figures.

DESCRIPTION OF PREFERRED EMBODIMENTS

Figure 1:
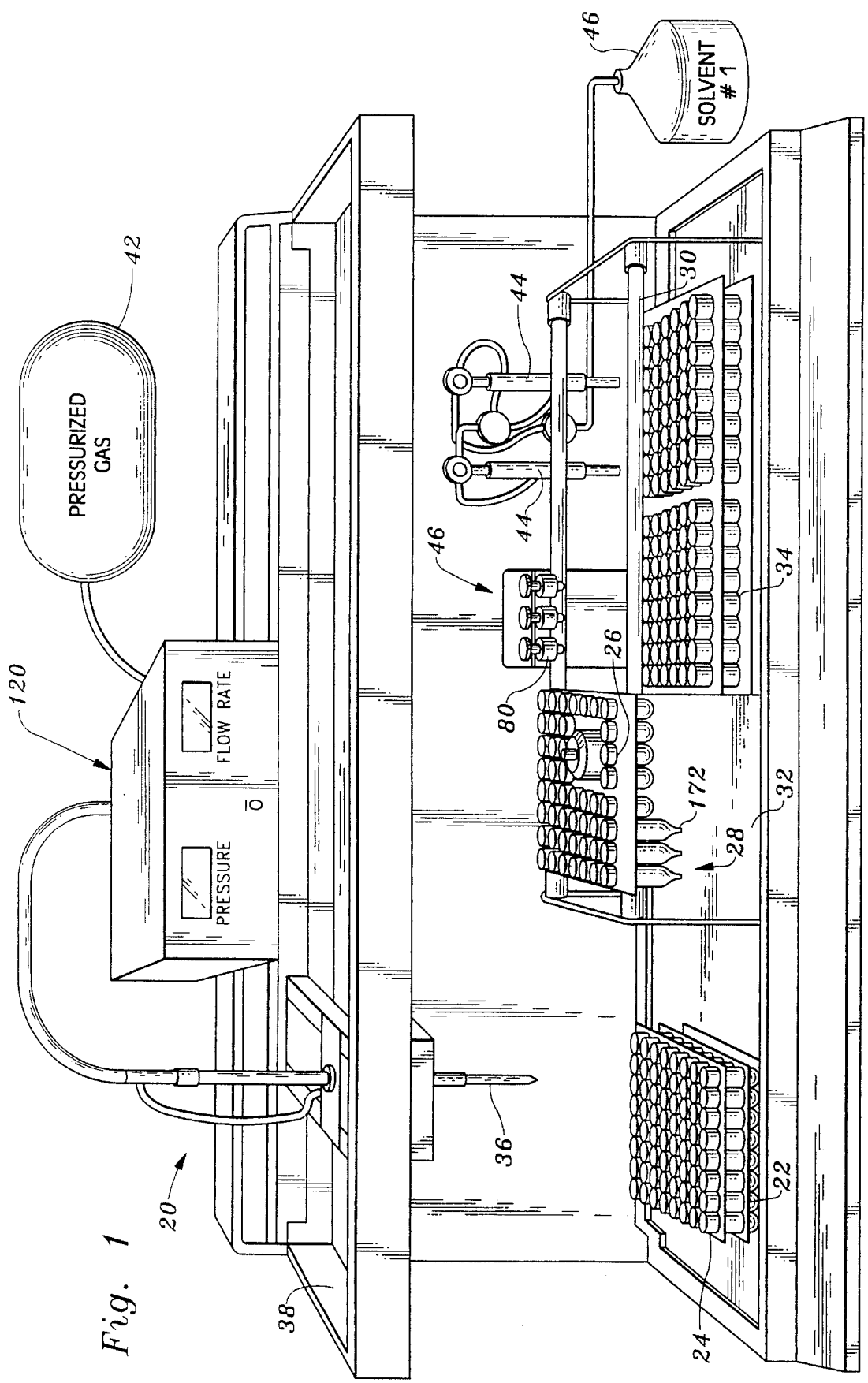
FIG. 1 is a perspective view of a liquid handling system and a fluid flow control system.

Considering the drawings, wherein like reference numerals denote like parts throughout the various drawing figures, reference numeral 120 is directed to the fluid flow control system according to the present invention.

Figure 2:
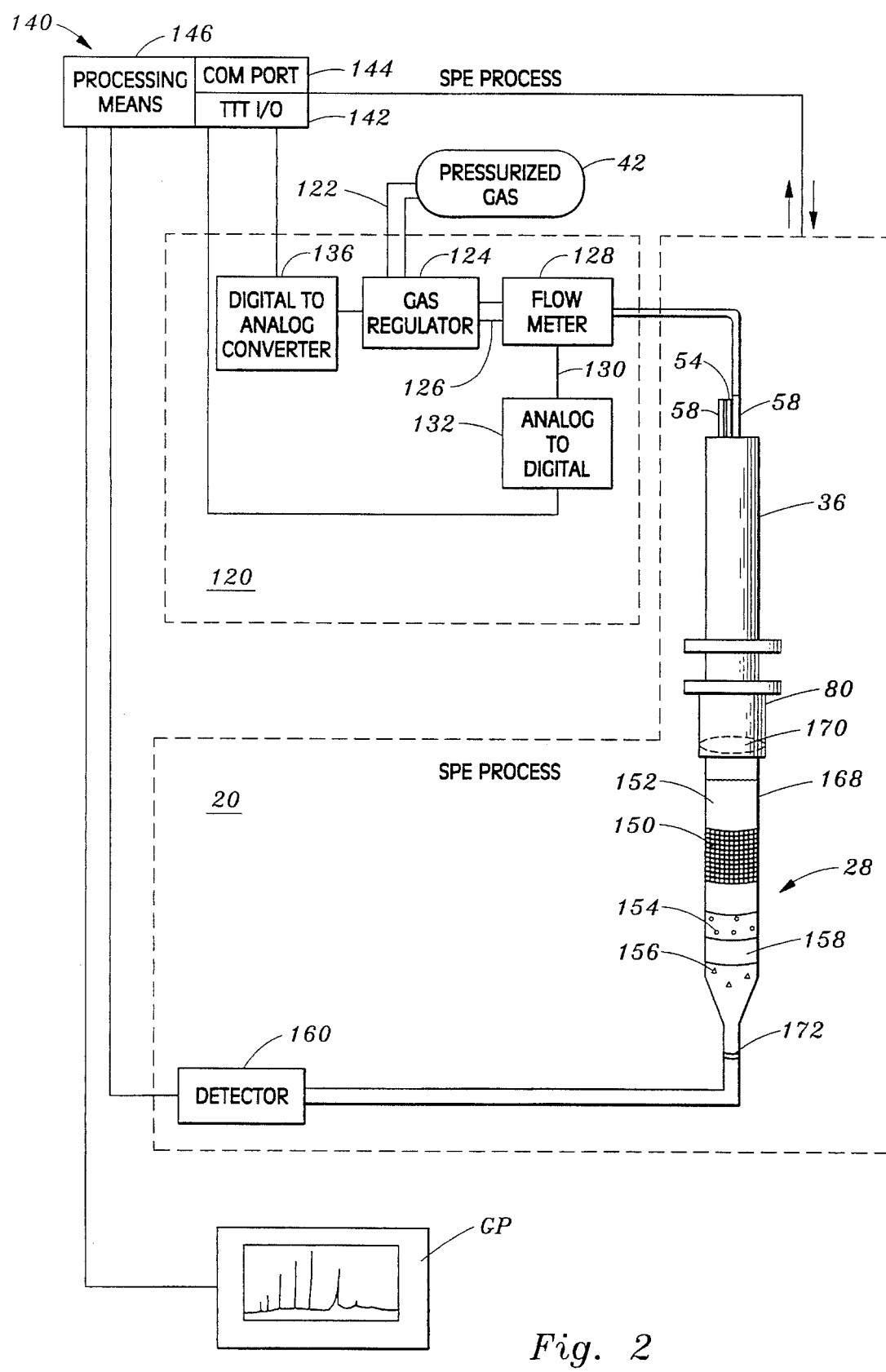
FIG. 2 is a block diagram of the fluid flow control system shown cooperating with a column.

In essence, and referring to FIGS. 1 and 2, a fluid flow control system 120 is provided which automatically monitors and optimizes fluid flow throughout a chromatographic process. For example, in high performance solid phase extraction methods, a column 28 (or tube 28) is provided having an internal stationary barrier or impediment 150, such as a frit, through which a sample 152, which includes the constituents to be separated, is initially disposed and adapted to be forced through the frit under pressure from a gas source. The sample 152 and the barrier 150 are serially stratified in the column 28. For a given sample, such as a blood specimen, a characteristic pressure curve is first called up from memory in a computer 140. As the sample is forced through the frit for analysis, the actual pressure used to move the sample is compared to the typical characteristic pressure curve to maximize cycle efficiency.

FIG. 1 depicts a liquid handling system 20, in this case specifically tailored for a preferred solid phase extraction (SPE) procedure, but not limited to such application. The system 20 includes a sample rack template 22 with space for a plurality of sample containers 24. A column carrier rack 26 receives a plurality of SPE columns 28. The column carrier rack 26 is mounted on a column switching platform 30, which permits the columns 28 to be moved horizontally between a waste collection tray 32 and a set of fraction collection containers 34. The sample containers 24, SPE columns 20, and fraction collection containers 34 are all supported in templates so that the precise location of the containers 24 an 34 and column 20 are established.

The liquid handling system permits a wide range of liquid handling operations. To transfer liquids, add liquids, and pressurize the SPE columns 20, a probe 36 is mounted on an x-y-z translator mechanism 38 above the structure described in the prior paragraph. The probe 36 may be translated in the x and y dimensions above the structure, and the probe 36 may be raised and lowered in the z dimension. Liquids such as solvents and gas pressure are supplied to the probe from liquid sources 40 and a pressurized gas source 42. Liquid is driven into the probe 36 through syringes 44 that precisely meter the amounts of liquids. This is delineated in our U.S. Pat. No. 5,324,480.

Figure 4:
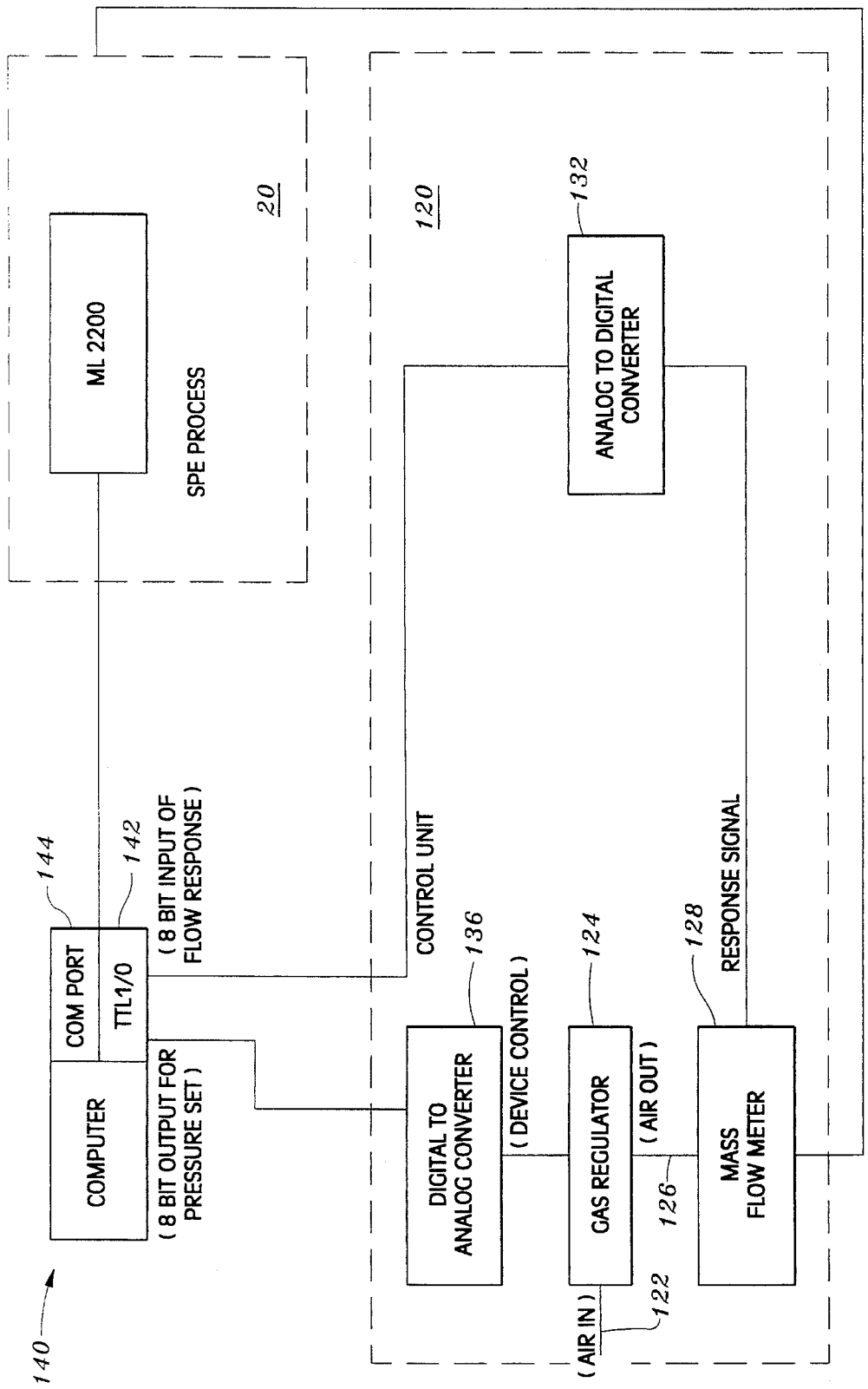
FIG. 4 is a block diagram of the fluid flow control system, a computer and (SPE) system.

More specifically and referring to FIG. 2 and 4, a column 28 comprised of a column body 168 includes upper and lower open ends 170, 172. The column 28 is provided with an internal impediment 150. A sample 152 is received within the interior of the column 28 and is situated between the upper open end 170 and impediment 150. A source of pressurized gas 42 is provided to a peripheral lumen 58 of a probe 36 and the probe 36 is coupled to the upper open end 170 of the column 28 by way of a seal head 80. In addition, other peripheral lumens 58 communicate with respective liquid sources either through a pump or through one of the syringes 44. Alternatively, some of the peripheral lumens 58 may be in communication with a source of other pressurized gas. The central lumen 54 acts in the manner of a needle to precisely dispense fluids.

The fluid flow control system 120 is interposed between the source of pressurized gas 42 and the probe 36. The fluid flow control system 120 includes a gas regulator 124, a flow meter 128 and means to continuously monitor and optimize the gas pressure and to subsequently monitor and optimize the sample 152 passing through the impediment 150.

Still more specifically, and referring to FIGS. 1 and 2, a fluid flow control system 120 is operatively coupled to a liquid handling system 20 which is, for example, tailored for performing solid phase extraction (SPE) procedures. Solid phase extraction often requires multiple steps such as column conditioning, sample loading, washing and elution. Depending on the application, the solvents and samples may have different viscosities, different constituents and, depending on the protocol step, may require different pressures.

The fluid flow control system 120 precisely provides and controls, inter alia, the various ranges of pressure required during the protocol steps which are critical in obtaining good recovery and throughput in (SPE) procedures. For example, and referring to FIG. 2, the elution of samples is typically carried out with a column 28 provided with an internal substantial stationary impediment or barrier 150, through which a sample 152 is pumped under pressure. Typically, impediments 150 may include packings such as sand, ceramics, frits, etc. as is known in the art. The sample 152 may have a variety of constituents which are intended to pass through the impediment 150 at different rates. For example, a distinct zone of the fastest moving constituents which have passed through the impediment 150 may be represented by triangles 156 and a subsequent zone of the next fastest moving constituents passing through the impediment 150 may be represented by circles 154 and so forth. As individual constituents of a sample 152 leave the column 28, a detector 160 is provided which detects the constituents by, for example, their absorption of ultraviolet light. The appearance of each component of a sample may then be recorded automatically, for example on graph paper GP.

The flow control system 120 senses the sequential throughput of the constituents of the sample 152 beyond the barrier 150 which initially impedes the sample 152. A source of pressurized gas 42 is operatively coupled to the probe 36 which in turn connects to the upper open end 170 of the column 28. The probe 36 couples to a seal head 80 which provides the means to connect the probe 36 to the column 28.

The gas regulator 124 of the flow control system 120 receives its commands from a processor 140, such as a computer. The command is preferably affected through a TTL input/output card 142 cooperating with the processing means 146 and the actual software package protocol. One particular TTL input/output card, such as that manufactured by Burr-Brown, provides an eight bit digital signal initiated from the software package and is capable of providing two hundred and fifty-five (255) equal pressure increments throughout the range of the gas regulator 124. A typical range of the gas regulator 124 is between zero (0) and thirty (30) pounds per square inch with an accuracy of zero point one percent (0.1%) of the full scale range. A typical gas regulator with the above characteristics is manufactured by Proportion-Air, Inc., McCordsville, Ind., Model Number QB1.

The eight bit digital signal is outputted by the TTL card to a digital to analog converter 136. This converter converts the 8 bit digital signal to an analog signal which is used to control the gas regulator 124. The gas regulator 124 receives gas in from the gas source 42 and exhausts gas out to a mass flow meter 128. The pressure at which the gas is exhausted from the gas regulator 124 is controlled by the analog signal which has been converted from the digital signal sent from the TTL input/output card 142. As a result, the gas pressure has a specific set point which is controlled by the processing means 140 through a specifically designed software package. This regulated gas pressure is sent through the flow meter 128 and downstream through a tube 68 and a peripheral lumen 58 of the probe 36 to the column 28 where the gas coacts with the sample 152 to push the sample 152 through the barrier 150 such that the individual constituents 154, 156 are separated therefrom. A typical flow meter is manufactured by AALBORG in Monsey, N.Y.

When the source of pressurized gas 42 provides a motive means to push the sample through the barrier 150, a back pressure develops which is correlative to the flow of the constituents 154, 156 past the barrier 150. This back pressure causes a change in the pressure of gas tending to flow through the flow meter 128. The flow meter 128 outputs the differential change in the gas pressure to an analog to digital converter 132. The analog to digital converter 132 converts the analog signal representative of the differential change in gas flow provided by the flow meter 128 to a digital signal.

This digital signal is transmitted to the TTL input/output 142 which cooperates with the processing means and the actual software package protocol to automatically monitor and optimize sample flow and the constituents 154, 156 during a chromatographic process. In essence, this forms a closed loop flow control system for (SPE) procedures.

One analogy on how the gas regulator 124 adjusts is through a load change. For example, if the gas pressure decreases downstream from the gas regulator 124, the regulator 124 will increase the flow to keep the set pressure point; if the gas pressure increases downstream from the gas regulator 124, the regulator 124 will decrease flow to keep the set pressure point.

This differential change in flow rate is correlative to the amount of resistance or impedance which the sample 152 sees when it is being pushed through the barrier 150. Therefore, the ability to monitor and optimize the gas pressure allows the throughput of a sample 152 beyond a barrier 150 to also be monitored and optimized. In other words, the flow rate and the differential changes in the flow rate of the sample 152 beyond the barrier 150 is monitored and optimized by the flow control system 120 during the chromatographic process.

This ability to monitor the state of the column 28 is essential to increase product throughput, safety and ease of operation of a solid phase extraction automated system. The flow control system 120 allows effective monitoring of the sample through the column 28 and can determine whether the column is plugged or whether there is a leak in the system. Since fluid flow through solid phase extraction columns varies greatly by sample composition and from column to column, the end user will not be constrained, as is currently the case, by the worse sample or column. Thus, while one sample might take one hundred and twenty (120) seconds to process, another may take only ninety (90) seconds. The flow control system 120 can sense these process times thereby allowing an increase in throughput. In addition, the flow control system 120 makes it possible to sense the pressure drop that occurs when the colunm 28 empties of solvent.

Figure 3:
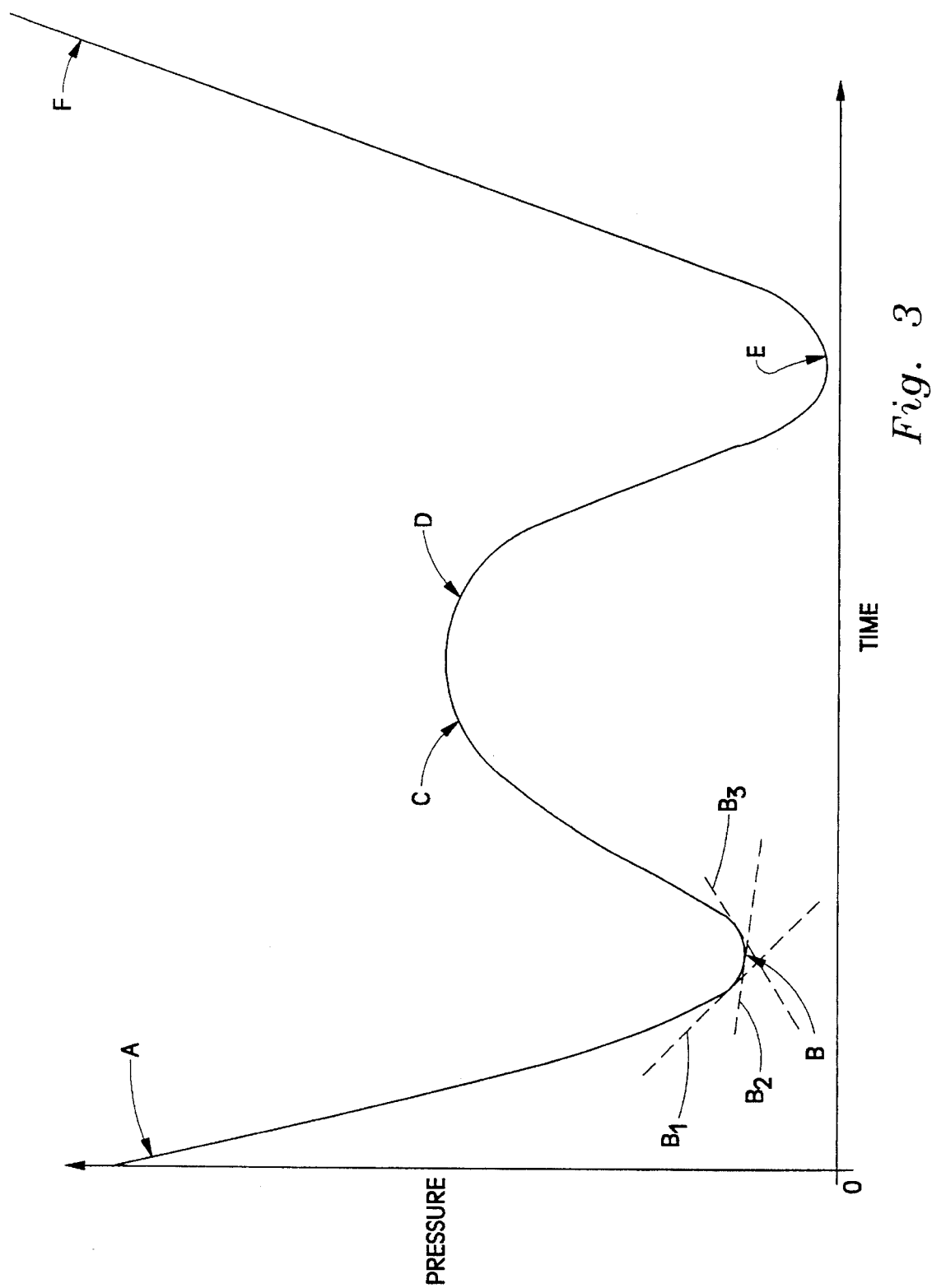
FIG. 3 is a pressure characteristic curve.

Referring to FIG. 3, a characteristic curve of pressure versus time is shown. At the time T equals zero, pressure is being provided to the column 28 which includes the sample 152 and the barrier 150 being stratified therein. At point A on the graph, a "cracking" pressure is provided in which a first constituent 156 starts to pass through the barrier 150. The pressure is backed off slightly so as not to push additional constituents through the barrier 150 too quickly. At point B on the curve, resistance to subsequent constituents passing therebeyond increases. Thus, pressure is increased to pass a further constituent 154 through the barrier 150. At point C, the pressure is maintained to provide a constant flow rate in order to push subsequent constituents through the barrier 150. Next, further constituents start to pass through the barrier 150 and a decrease in pressure results from a decrease in the resistance to the constituents passing through the barrier 150. The pressure may be backed off slightly so that this desired constituent may completely pass through the barrier without introducing additional constituents as a result of an increased pressure. Once the last desired constituent has passed through the barrier 150 the resistance of the barrier 150 diminishes greatly with respect to any remaining sample and thus, an extreme increase in pressure results as shown from point E to point F on the graph. This is a tell-tale sign of a completed chromatographic process.

In use and operation, to pick up a seal head 80 or other implement in the parking station 46, the probe 36 is moved into position over the seal head 80 by the x-y portion of the x-y-z translator. The z portion of the translator lowers the probe 36 into engagement with the seal head 80, and achieves locking engagement. The x-y y portion of the x-y-z translator moves the seal head 80 sideways to clear it from the parking station 46. The seal head is replaced onto the parking station 46 by reversing these steps. The probe 36 is withdrawn by the upward z-movement of the translator 38.

The present approach gives the liquid handling system great versatility in performing a wide variety of procedures. Liquids are drawn into the probe, transferred, and other liquids added. Containers may be safely pressurized. A wide range of standardized containers and columns may be used, due to the versatility of the seal head design and the use of the parking station. Auxiliary implements such as filters may also be engaged to the probe and utilized.

Figure 5:
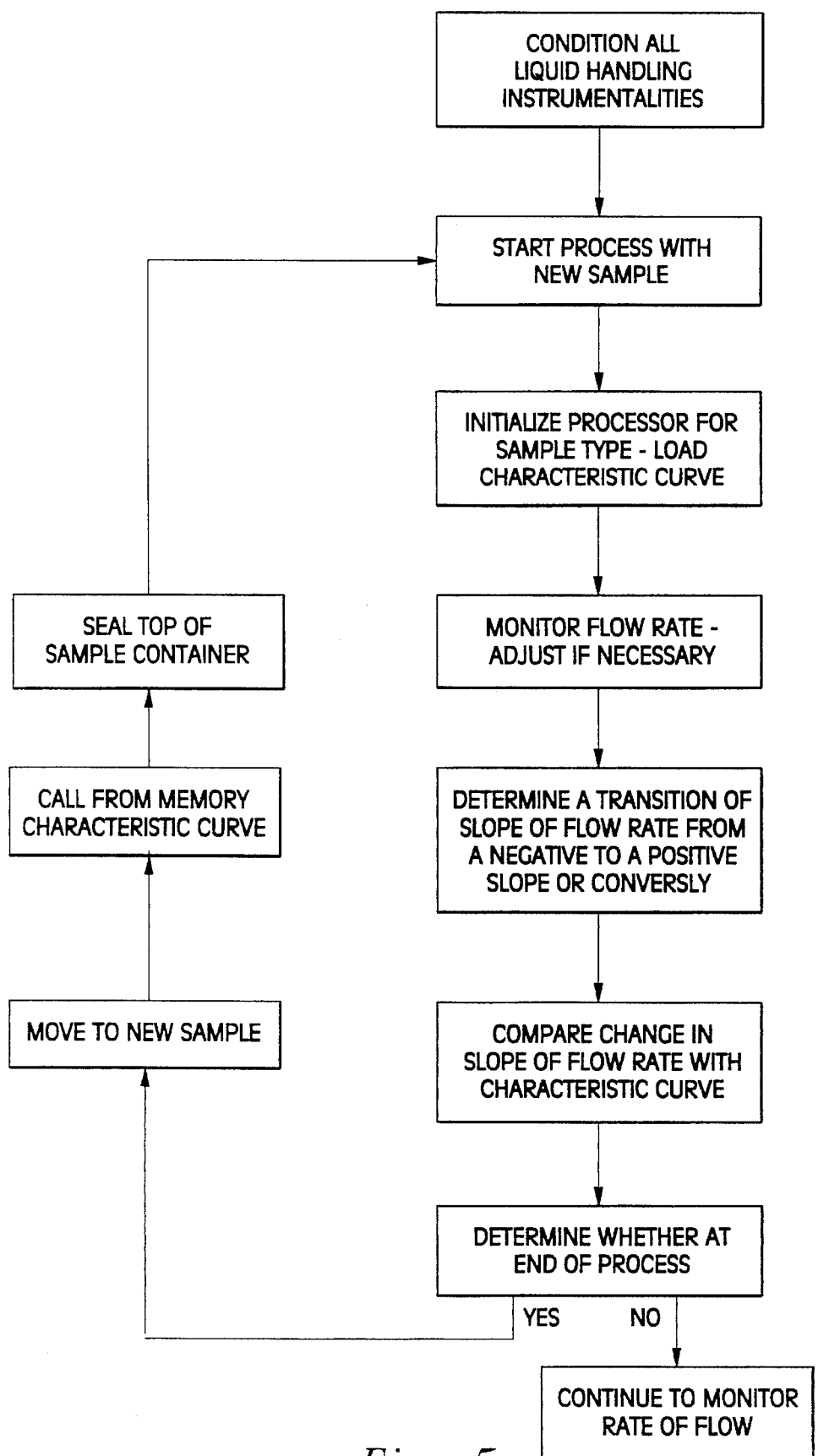
FIG. 5 is a basic block diagram of the (SPE) process being carried out.

Referring to FIG. 5, the basic steps in eluting a sample are outlined. At the outset, all liquid handling chambers, sample containers and fraction collection containers are conditioned, which may include a washing step. The computer 140 is initialized for sample type and a characteristic pressure curve is loaded into memory. The SPE process is then initiated and the pressure flow rate is monitored and controlled by the fluid flow control system. Referring to FIG. 3, a transition of slope on the pressure curve is analyzed and compared with the characteristic curve. For example, the transition of slope from a negative slope $B_1$ to a zero slope $B_2$ and then to a positive slope $B_3$ is analyzed and compared with the characteristic curve to determine a characteristic of the sample. At point C the transition of the slope is converse, from a positive slope to a zero slope and then to a negative slope. This transition is also analyzed and compared with the characteristic of the sample. This process continues throughout a run and is particularly important in determining when the last desired constituent has passed through the barrier to determine the end of the run or process. Upon completion of a particular process a new process may be initiated with a new sample and if needed a new characteristic curve.

Moreover, having thus described the invention, it should be apparent that numerous structural modifications and adaptations may be resorted to without departing from the scope and fair meaning of the instant invention as set forth here in above and as described here in below by the claims.

We claim:

1. A chromatographic device comprising, in combination:

a sample holder;

a sample having a plurality of constituents;

a chromatographic barrier;

said sample and said barrier stratified in said sample holder in which said sample is initially impeded by said barrier;

pressure means operatively coupled to said sample holder to push said sample beyond said barrier to a detector;

means to adjust said pressure means;

and means to sense flow rate of each said constituent of said sample as it passes through said barrier, control means for providing a closed feedback loop to operatively couple said flow rate sensing means to said pressure adjusting means whereby the means to adjust the pressure means is controlled in response to sensed flow rate;

whereby as said flow rate sensing means denotes passage of one of said plural constituents beyond said barrier, said one constituent passes to said detector for analysis.

2. The device of claim 1 wherein said pressure adjusting means includes a regulator operatively coupled to said pressure means and said sample holder for receiving gas from said pressure means and exhausting gas to said sample holder.

3. The device of claim 2 wherein said control means includes processing means for accessing a characteristic pressure curve characteristic of passing said sample through said barrier.

4. The device of claim 3 wherein said control means includes means for receiving and applying a control signal from said processing means to said regulator wherein the control signal provides a set point from said processing means at which the gas is exhausted from said regulator.

5. The device of claim 4 wherein said means to sense flow rate includes a flow meter operatively coupled between said regulator and said sample holder.

6. The device of claim 3 wherein said flow meter monitors a differential change in the pressure through said flow meter correlative to the passage of the constituents of said sample through said barrier.

7. The device of claim 6 wherein said flow meter includes means for providing an output signal proportional to the differential change in pressure.

8. The device of claim 7 including means for receiving and applying the output signal from the flow meter to the processing means.

9. The device of claim 8 wherein the processing means compares the output signal with the characteristic pressure curve and automatically adjusts the control signal to optimize the flow of the constituents of said sample past said barrier.

10. A device for sensing the throughput of a sample beyond a chromatographic barrier in which the sample is initially impeded by said barrier from flowing with respect to a detector, said device comprising, in combination:

a gas source;

a gas regulator having an input operatively coupled to said gas source and an output;

means to control the pressure at which the gas is exhausted from the output of said gas regulator;

a column having a chromatographic barrier and a sample stratified therein, a flow meter operatively coupled both to said column in which the sample and said barrier are stratified and to the output of said gas regulator for monitoring the flow of gas coacting with said sample;

means for determining a resultant differential change in pressure correlative to the flow of constituents of the sample past said barrier;

said flow meter including means to output the resultant differential change in pressure to said control means forming a closed feedback loop system;

wherein said flow of the sample beyond said barrier to said detector is automatically monitored and optimized from beginning to end of a chromatographic process.

11. A chromatographic apparatus comprising, in combination:

a sample column;

a sample and a chromatographic barrier serially stratified in said sample column;

a source of pressurized gas;

a gas regulator operatively coupled to said source of pressurized gas and having an output;

a flow meter operatively coupled between said output of said gas regulator and said column for monitoring a change in the pressure correlative with the through passage of the sample beyond said barrier throughout a chromatographic process;

a processing means;

a closed feedback loop means operatively coupled between said flow meter and said processing means for controlling said output of said gas regulator;

whereby the throughput of the sample beyond said barrier is automatically monitored and optimized throughout a chromatographic process.

12. The apparatus of claim 11 wherein said processing means includes means for selecting from a memory a characteristic pressure curve correlative of passing the sample through said barrier.

13. The apparatus of claim 12 further including means for developing a sample pressure curve from said means for monitoring a change in the pressure correlative with the through passage of the sample beyond said barrier throughout the chromatographic process.

14. The apparatus of claim 13 further including means for comparing a transition of slope on the sample pressure curve with a transition of slope on said characteristic pressure curve to optimize cycle time for assaying the sample.

* * * * *